United States Patent [19]

Mallion

[11] Patent Number: 5,096,918
[45] Date of Patent: Mar. 17, 1992

[54] ISOINDOLINE NITROMETHANE DERIVATIVES

[75] Inventor: Keith B. Mallion, Knutsford, Great Britain

[73] Assignee: Imperial Chemical Industries PLC, London, England

[21] Appl. No.: 474,935

[22] Filed: Feb. 5, 1990

[30] Foreign Application Priority Data

Feb. 3, 1989 [GB] United Kingdom ............... 8902405

[51] Int. Cl.$^5$ .................. A61K 31/40; C07D 209/44
[52] U.S. Cl. .................... 514/416; 540/203;
540/593; 540/604; 544/52; 544/58.2; 544/105;
544/353; 544/383; 544/160; 546/141; 546/153;
546/232; 546/248; 548/146; 548/1768;
548/179; 548/207; 548/214; 548/470; 548/482;
548/491; 548/542
[58] Field of Search ................ 548/470, 482; 514/416

[56] References Cited

U.S. PATENT DOCUMENTS 4,053,633 10/1977 Goralski et al. ..................... 71/67

FOREIGN PATENT DOCUMENTS 0304190 2/1989 European Pat. Off. .
1229653 4/1971 United Kingdom ............... 548/470

OTHER PUBLICATIONS

J. Organic Chemistry, 43:3101 (1978).
J. Prakt. Chem., 101:136–157 (1920) (Chemical Abstracts, vol. 15, pp. 1013–1014.
Rec. Trav. Chim. Pays Bas., 93:11–14 (1974).
Chemical Abstracts, vol. 59, Abstract No. 6341g.
J. Polymer Science, Polymer Chemistry Edition, 23:1963–1972 (1985).
J. Heterocyclic Chemistry, 14:1415–1416 (1977). )
Tetrahedron, 25:181–189 (1969).

Primary Examiner—C. Warren Ivy
Assistant Examiner—James H. Turnipseed
Attorney, Agent, or Firm—Cushman, Darby & Cushman

[57] ABSTRACT

The invention concerns pharmaceutically useful heterocyclic nitromethane compounds of the formula I:

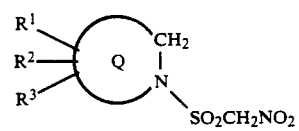

in which ring Q is a heterocycle of 4 to 7 ring atoms, the fragment completing the ring Q having 2 to 5 atoms, one of which is carbon, oxygen, sulphur or a group of the formula —NRa—, and the remainder are carbon; Ra is hydrogen, (1–6C)alkyl, (2–6C)alkanoyl, trifluoroacetyl, phenyl, benzoyl, or phenyl(1–4C)alkyl, the latter three optionally substituted; and $R^1$ $R^2$ and $R^3$ are independently hydrogen, hydroxy, (1–6C)alkyl, (1–6C)alkoxy, phenyl, phenoxy or phenyl(1–4C)alkyl, the last three optionally substituted, or two of $R^1$, $R^2$ and $R^3$ situated on adjacent ring carbon atoms and together with said carbon atoms form a benzene ring fused to ring Q, the benzene ring itself optionally substituted, provided that when the fragment completion ring Q is of 3 atoms then at least one of $R^1$, $R^2$ and $R^3$ is hydrogen; and salts thereof. Other aspects of the invention include the production of the novel compounds by analogy processes and pharmaceutical compositions of the novel compounds and of N-(nitromethylsulphonyl)-morpholine for use in the treatment of diabetic complications.

5 Claims, No Drawings

ISOINDOLINE NITROMETHANE DERIVATIVES

TECHNICAL FIELD

This invention concerns novel heterocyclic nitromethane derivatives which are inhibitors of the enzyme aldose reductase and which are of value, for example, in the treatment of certain peripheral effects of diabetes or galactosemia. A method of treating one or more of such peripheral effects using a heterocyclic nitromethane derivative and pharmaceutical compositions containing such a derivative are also provided. In addition the invention concerns novel processes for the manufacture of the said novel derivatives and for the preparation of medicaments containing any of the nitromethane derivatives.

BACKGROUND TO INVENTION

The enzyme aldose reductase is responsible for the catalytic conversion of aldoses, such as glucose and galactose, to the corresponding alditols, such as sorbitol and galactitol respectively, in warm blooded animals such as man. Alditols penetrate cell membranes poorly and, once formed, tend to be removed only by further metabolism. Consequently, alditols tend to accumulate within cells where they are formed, causing a rise in internal osmotic pressure which may in turn be sufficient to destroy or impair the function of the cells themselves. In addition, raised alditol levels may result in abnormal levels of their metabolites which may themselves impair or damage cellular function. The enzyme aldose reductase has a relatively low substrate affinity and is generally only effective in the presence of relatively large concentrations of aldose. Such large concentrations are present in the clinical conditions of diabetes (excessive glucose) and galactosemia (excessive galactose). Consequently, aldose reductase inhibitors are useful in the reduction or prevention of the development of those peripheral effects of diabetes or galactosemia which may be due in part to the accumulation of sorbitol or galactitol, respectively, in tissues such as the eye, nerve and kidney. Such peripheral effects include, for example, macular oedema, cataract, retinopathy, neuropathy and impaired neural conduction.

Although a number of aldose reductase inhibitors have been discovered and clinically evaluated, there is a continuing need for alternative inhibitors. The present invention is based in part on this need and on our discovery of the unexpected inhibition of the enzyme aldose reductase by certain heterocyclic nitromethane derivatives defined below. A structurally related compound, N-(nitromethylsulphonyl)morpholine, has been described, together with the preparation of its lithium salt, by Truce and Christensen (Tetrahedron, 1969, 25, 181–189) but without indication of any useful pharmacological properties.

DISCLOSURE OF INVENTION

According to the invention there is provided a heterocyclic compound of the formula I (set out hereinafter at the end of the Examples together with the other chemical formulae appearing in Roman numerals) wherein ring Q is a saturated or partially unsaturated heterocycle of 4 to 7 ring atoms, in which the fragment completing the ring is of 2 to 5 atoms, one of which is carbon, oxygen, sulphur or a group of the formula —NRa—, and the remainder are carbon; Ra is hydrogen, (1-6C)alkyl, (2-6C)alkanoyl, trifluoroacetyl, phenyl, benzoyl, or phenyl(1-4C)alkyl, the latter three optionally bearing 1 or 2 substituents independently selected from halogeno, trifluoromethyl, (1-4C)-alkyl and (1-4C)alkoxy; and $R^1$, $R^2$ and $R^3$ are independently selected from hydrogen, hydroxy, (1-6C)alkyl, (1-6C)alkoxy, phenyl, phenoxy and phenyl(1-4C)alkyl, the last three of which may themselves optionally bear 1 or 2 substituents independently selected from halogeno, trifluoromethyl, (1-4C)alkyl and (1-4C)alkoxy, or two of $R^1$, $R^2$ and $R^3$ situated on adjacent ring carbon atoms and together with said carbon atoms form a benzene ring fused to ring Q, the benzene ring itself optionally bearing 1 or 2 substituents independently selected from halogeno and the previously defined values for $R^1$, $R^2$ and $R^3$ and provided that when the fragment completing ring Q is of 3 atoms then at least one of $R^1$, $R^2$ and $R^3$ is hydrogen; or a pharmaceutically acceptable salt thereof; but excluding the compound N-(nitromethylsulphonyl)morpholine and its lithium salt.

In this specification the term "alkyl" includes both straight and branched alkyl groups but references to individual alkyl groups such as "propyl" are specific for the straight chain ("normal") version only, any branched chain isomer such as "isopropyl" being referred to specifically. An analogous convention applies to other generic terms.

It is to be understood that, insofar as certain of the compounds of formula I defined above may exist in optically active or racemic forms by virtue of one or more substituents containing an asymmetric carbon atom, the invention includes any such optically active or racemic form which possesses the property of inhibiting the enzyme aldose reductase. The synthesis of optically active forms may be carried out by standard techniques of organic chemistry well known in the art, for example by synthesis from optically active starting materials or by resolution of a racemic form. Similarly, inhibitory properties against aldose reductase may be evaluated using standard laboratory tests, for example those referred to hereinafter.

Particular values for the group Ra include, for example:
for (1-6C)alkyl: (1-4C)alkyl, methyl, ethyl, isopropyl and propyl;
for (2-6C)alkanoyl: (2-4C)alkanoyl, such as acetyl, propionyl and butyryl; and
for phenyl(1-4C)alkyl: phenylmethyl, 1-phenylethyl, 2-phenylethyl and 3-phenylpropyl.

Particular values for optional substituents which may be present when Ra is phenyl, benzoyl, or phenyl(1-4-C)alkyl, or when $R^1$, $R^2$ or $R^3$ is phenyl, phenoxy or phenyl (1-4C)alkyl or on a benzene ring fused to ring Q include, for example:
for (1-4C)alkyl, methyl, ethyl, isopropyl and propyl;
for (1-4C)alkoxl, methoxy, ethoxy and propoxy; and
for halogeno, fluoro, chloro, bromo and iodo.

Particular values for $R^1$, $R^2$ or $R^3$ (or for optional substituents present on a benzene ring fused to ring Q) include, for example:
for (1-6C)alkyl, methyl, ethyl, isopropyl, propyl and butyl;
for (1-6C)alkoxy, methoxy, ethoxy, propoxy, butoxy and t-butoxy;
for phenyl(1-4C)alkyl, benzyl, 1-phenylethyl and 2-phenylethyl.

Specific values for the ring moiety Q include, for example, azetidino, pyrrolidino, piperidino, piperazin- 1-yl, thiazolidino, 1-azacyclohept-1-yl, 1,2,3,4-tetrahydropyridin-1-yl, morpholino and thiomorpholino, to any of which a benzene moiety formed from two of $R^1$, $R^2$ and $R^3$ on adjacent carbon atoms of Q may be fused, said benzene moiety being optionally substituted as defined above.

A particular group of compounds of the invention comprises compounds of the formula II wherein X is oxygen, sulphur or a group of the formula —NRa— or a group of the formula —$CHR^4$— in which is hydrogen or (1–4C)alkyl, $R^5$ and $R^6$ are independently hydrogen or (1–4C)alkyl located on any ring carbon atom except that marked with an asterisk (*), n and m are independently zero or the integers 1, 2 or 3, such that together they total 1, 2 or 3, (.) stands for a ring methylene group, and Ra has any of the meanings defined hereinabove; together with the pharmaceutically acceptable salts thereof; but excluding the compound N-(nitromethylsulphonyl)morpholine and its lithium salt.

A particular value for $R^4$, $R^5$ or $R^6$ when it is (1–4C)alkyl is, for example, methyl or ethyl.

A further particular group of compounds of the invention comprises compounds of the formula III wherein one of A and B is methylene, ethylene or a direct bond and the other is a group of the formula >N—$SO_2CH_2NO_2$, $R^7$ is a substituent optionally present on a methylene in the ring containing A and B, said optional substituent being selected from any of the values defined hereinbefore for $R^1$, $R^2$ or $R^3$ alone, and $R^8$ and $R^9$ are independently selected from hydrogen, hydroxy, (1–4C)alkyl, (1–4C)alkoxy and halogeno; together with the pharmaceutically acceptable salts thereof.

Within the above group, a particularly preferred group comprises those compounds in which A is methylene and B is a group of the formula >N—$SO_2CH_2NO_2$, that is 1,2,3,4-tetrahydroisoquinolines of the formula IV in which $R^7$, $R^8$ and $R^9$ may have any of the above defined meanings, together with the pharmaceutically acceptable salts thereof.

Compounds of particular interest are described in the accompanying Examples and are provided, together with their pharmaceutically acceptable salts, as a further feature of the invention. Of these compounds, those described in Examples 2, 3, 13, 15 and 18 are of special interest and are provided, together with the pharmaceutically acceptable salts thereof, as a separate feature of the invention.

The invention further comprises pharmaceutical compositions comprising a compound of the formula I or a pharmaceutically acceptable salt thereof, as defined above, together with a pharmaceutically acceptable diluent or carrier. The invention also includes pharmaceutical compositions comprising N-(nitromethylsulphonyl)morpholine or a pharmaceutically acceptable salt thereof, together with a pharmaceutically acceptable diluent or carrier.

The compositions of the invention may be in various conventional forms. Thus, they may be in a form suitable for oral use (for example as tablets, lozenges, hard or soft capsules, aqueous or oily suspensions, emulsions, dispersible powders or granules, syrups or elixirs), for topical use (for example as creams, ointments, gels or aqueous or oily solutions or suspensions) or for parenteral administration (for example as a sterile aqueous or oily solution for intravenous, subcutaneous, intramuscular or intravascular dosing) or as a suppository for rectal dosing.

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or alginic acid; binding agents such as gelatin or starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as arachis oil, liquid paraffin or olive oil.

Aqueous suspensions generally contain the active ingredient in finely powdered from together with one or more suspending agents, such as sodium carboxymethylcellulose, methylcellulose, hydroxypropylmethylcellulose, sodium alginate, polyvinylpyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharin or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occuring gums such as gum acacia or gum tragacanth, naturally-occurring phosphatides such as soya bean, lecithin, or esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art. Topical formulations for administration to the eye will generally be in the form of an ointment, gel or sterile solution buffered at an ophthalmically acceptable pH, for example in the range pH 7.0-7.6.

The amount of active ingredient that is combined with one or more excipients to produce a single dosage form will necessarily vary depending upon the host treated and the particular route of administration. For example, a formulation intended for oral administration to humans will generally contain for example from 0.5 mg to 1 g of active agent compounded with an appropriate and convenient amount of excipients which may vary from about 5 to about 98 percent by weight of the total composition. Dosage unit forms will generally contain about 1 mg to about 500 mg of an active ingredient.

Suitable pharmaceutically acceptable salts include, for example, alkali metal (such as potassium or sodium), alkaline earth metal (such as calcium or magnesium) and ammonium salts, and salts with organic bases affording physiologically acceptable cations, such as salts with methylamine, dimethylamine, trimethylamine, piperidine and morpholine.

The novel compounds of the invention may be obtained by standard procedures of organic chemistry already known for the production of structurally analogous compounds. Such procedures are provided as a further feature of the invention and are illustrated by the following preferred procedure in which the generic radicals have any of the meanings defined hereinbefore.

A sulphone of the formula V is reacted with a (1-5-C)alkyl nitrate, such as ethyl, propyl, isobutyl or isoamyl nitrate, in the presence of a strong base.

This process is particularly suited to the production of those compounds of formula I in which Ra is other than (2-6C)-alkanoyl or benzoyl.

A particularly suitable strong base is, for example, an alkali metal (1-6C)alkane such as butyllithium.

The reaction is preferably carried out in the presence of a suitable solvent or diluent, for example an ether such as tetrahydrofuran or t-butyl methyl ether, and at a temperature in the range, for example, $-80°$ to $10°$ C.

The necessary sulphones of the formula V may be made by standard procedures well known in the art, for example by reaction of the corresponding cyclic amine of the formula VI with methanesulphonyl chloride in the presence of a suitable base such as triethylamine or N-methylmorpholine in a suitable solvent or diluent such as toluene or t-butyl methyl ether and at a temperature in the range, for example, $-10°$ to $30°$ C.

It will be appreciated that in the formula I compounds of the invention Q may bear a number of reactive substituents. Accordingly, it may be necessary to protect one or more such reactive substituents in a conventional manner at some stage prior to carrying out the above procedures and then to remove the protecting group as a final step. Thus, for example, a hydroxy substituent may be protected using, for example, a tetrahydropyranyl, t-butyl, allyl or benzyl protecting group.

The appropriate protecting groups and the procedures necessary for the protection and deprotection of reactive substituents are well described in standard text-books of organic chemistry. The invention includes a development of the above process for the production of a novel compound of formula I, as defined hereinbefore, which is characterised by using a starting material of the formula V in which one (or more) of any reactive substituents present has been protected with an appropriate protecting group, and carrying out the appropriate removal of the protecting group as a final step.

It will be appreciated that those compounds wherein Ra is alkanoyl, trifluoroacetyl or benzoyl, the above process is generally carried out with a compound of formula I in which Ra is hydrogen followed by conventional acylation of the initial reaction product. Such procedures and their reverse (that is hydrolysis and deacylation) are provided as further features of the invention.

Whereafter, when a pharmaceutically acceptable salt is required, a compound of formula I may be reacted with an appropriate base having a non-toxic cation.

As stated previously, the compounds of formula I inhibit the enzyme aldose reductase. The compounds are thus of value, for example, in treating those diseases or conditions which are caused by excessive quantities of the products such as sorbitol formed in the body by processes catalysed by the enzyme aldose reductase, for example in treating the peripheral side effects of diabetes.

The property of inhibiting the enzyme aldose reductase in vivo may be demonstrated in the following standard laboratory test. Thus, rats are made diabetic (as evidenced by severe glucosuria being present) by dosing with streptozotocin. The animals are then dosed daily with the test compound for one, two or five days. The animals are then killed 2-6 hours after the final dose and the eye lenses and/or sciatic nerves are removed. After a standard work-up procedure the residual sorbitol levels in each tissue are determined by gas liquid chromatography after conversion to the poly-trimethylsilyl derivatives. Inhibition of aldose reductase in vivo is then assessed by comparing the residual sorbitol levels in tissues from the dosed diabetic group of rats with those of an undosed group of diabetic rats and an undosed, normal group of rats.

The property of inhibiting the enzyme aldose reductase may also be demonstrated in vitro. Thus, partially purified aldose reductase is isolated in known manner from bovine lenses. The percentage inhibition of this enzyme's ability in vitro to catalyse the reduction of aldoses to polyhydric alcohols, and particularly to reduce glucose to sorbitol, caused by a test compound is then determined using standard spectrophotometric methods.

By way of illustration of the aldose reductase inhibitory properties of compounds of formula I, the compound of Example 1 had an $IC_{50}$ of $33 \times 10^{-8}M$ in the above in vitro test. Similarly, the known compound N-(nitromethylsulphonyl)morpholine has an $IC_{50}$ of $88 \times 10^{-8}M$ in the above in vitro test. In general, compounds of the formula I show significant inhibition in the above mentioned in vivo test at a dose (generally p.o.) of 100 mg/kg or much less with no evidence of overt toxicity, and have an $IC_{50}$ in the above mentioned in vitro test of $10^{-5}M$ or much less.

The compounds of formula I will primarily be administered systemically (generally by mouth) to a warm-blooded animal to produce a therapeutic or prophylactic effect mediated by inhibition of the enzyme aldose reductase, for example at a daily dose in the range of 1 to 40 mg/kg. In man it is envisaged that a total daily dose in the range 15 to 800 mg. per man will be administered, given if necessary, in divided doses.

However, the precise amount of compound administered will naturally vary somewhat, for example, with the age and sex of the patient and the severity and extent of the condition being treated.

The compounds of formula I may also be administered topically, for example by topical administration direct to the tissue or organ in which inhibition of the enzyme is required, for example by topical administration to the eye. The precise amount of compound administered will necessarily depend on the formulation used. Thus, for example, when a solution is administered a concentration of the compound containing up to 0.01% by weight will generally be used. Similarly, when an ointment is administered a concentration of the compound of up to 2% by weight will generally be used. Topical formulations of compounds of formula I may be administered to the eye of an animal, for example, man or dog, requiring treatment and/or prevention of diabetic cataracts or retinopathy, in a conventional manner, for example, using a drop or eyewash topical formulation.

The compounds of formula I may also be administered together with one or more other agents which are known to have a useful effect in the treatment of diabetes or galactosemia, for example a hypoglycaemic agent such as tolbutamide, chlorpropamide or glybenclamide.

The invention will now be illustrated by the following non-limiting Examples in which, unless otherwise stated:

(i) all evaporations were carried out by rotary evaporation in vacuo.

(ii) all operations were carried out at room temperature, that is in the range 18°-26° C.;

(iii) the purity of chemical products was assessed by nuclear magnetic resonance spectroscopy, mass spectroscopy, thin layer chromatographic analysis and/or microanalysis;

(v) yields are for illustration only and are not necessarily the maximum attainable by diligent process development.

EXAMPLES 1-12

The following is a general procedure for the preparation of the compounds of formula I:

A solution of the methylsulphonyl derivative of formula V (0.0613M) in dry tetrahydrofuran, (THF) (250 ml) was stirred under rigorously dry conditions under argon at about 0° C. whilst a solution of 1.6M butyllithium in hexane (50 ml, 1.29 equivalents) was added over 10 minutes. The clear solution was cooled to −30° C. and treated with isoamyl nitrate (8.19 ml, 8.16 g, 0.0613M) over about 10 minutes. The solution was stirred at about −30° C. for 4 hours and then treated with acetic acid (4.6 ml, 0.08 mole equivalent to the butyllitium used) and allowed to warm to ambient temperature. The solvent was evaporated and the residue partitioned between a 2:1 v/v mixture of ether and methylene chloride (1×150 ml, 1×50 ml) and a solution of sodium hydroxide (4.0 g) in water (90 ml).

The alkaline aqueous layer was stirred in an ice-bath and acidified to pH 5 by addition of acetic acid (7.5 ml). The material which separated was extracted with a 2:1 v/v mixture of ether and methylene chloride (1×100 ml, 1×50 ml). The combined organic layers were washed with water (40 ml), treated with activated carbon and dried (MgSO4) and then the solvent was evaporated. The residue was purified by chromatography on 10 times its weight of silica gel (Merck Art. 7734), eluting with methylene chloride and then recrystallising from an appropriate solvent.

In this manner, the following compounds of formula I were obtained. Any recrystallisation solvent is given in parentheses after melting point.

EXAMPLE 1

N-(nitromethylsulphonyl)piperidine, in 16% yield*, m.p. 95°-96° C. (1:1 v/v ethanol: water); microanalysis; found: C,34.7; H,5.8; N,13.6%; $C_6H_{12}N_2O_4S$ requires: C,34.6; H,5.8; N,13.4%; m/e 207 (M-H);

EXAMPLE 2

N-(nitromethylsulphonyl)pyrrolidine, in 19% yield* m.p. 110°-112° C. (ethanol); microanalysis, found: C,30.9; H,5.2; N, 14.5%; $C_5H_{10}N_2O_4S$ requires: C,30.9; H,5.2; N,14.4%; m/e 193 (M-H);

EXAMPLE 3

2-(nitromethylsulphonyl)-1,2,3,4-tetrahydroisoquinoline, in 21% yield**, m.p. 91°-92° C. (1:1 v/v ethanol: water); microanalysis, found: C,47.3; H,4.8; N,11.0%; $C_{10}H_{12}N_2O_4S$ requires: C,46.9; H,4.7; N,10.9%; m/e 274 (M+NH4)+;

EXAMPLE 4

1-(nitromethylsulphonyl)-1,2,3,4-tetrahydroquinoline, in 10% yield, m.p. 56°-58° C. (ethanol); microanalysis, found: C,47.1; H,4.8; N, 10.7%; $C_{10}H_{12}N_2O_4S$ requires: C,46.9; H,4.7; N,10.9%; m/e 274 (M+NH4)+;

EXAMPLE 5

N-(nitromethylsulphonyl)-4-phenylpiperidine, in 13% yield, m.p. 151°–152° C. (ethanol); microanalysis, found: C,50.8; H,5.8; N,9.8%; $C_{12}H_{16}N_2O_4S$ requires: C,50.7; H,5.7; N,9.9%; m/e 302 $(M+NH_4)^+$;

EXAMPLE 6

N-(nitromethylsulphonyl)thiomorpholine, in 20% yield m.p. 114°–115° C. (ethanol); microanalysis, found: C,26.7; H,4.4; N,13.2%; $C_5H_{10}N_2O_4S_2$ requires: C,26.5; H,4.45; N,13.2%; m/e 226 $M^+$;

EXAMPLE 7

N-(nitromethylsulphonyl)thiazolidine, in 9% yield, m.p. 75°–76° C.; microanalysis, found: C,22.6; H,3.7; N,13.2%; $C_4H_8N_2O_4S_2$ requires: C,22.6; H,3.8; N,13.25; m/e 230 $(M+NH_4)^+$;

EXAMPLE 8

2,6-dimethyl-N-(nitromethylsulphonyl)piperidine, in 30.4% yield, m.p. 76.5°–78° C. (50% aqueous ethanol); microanalysis, found: C, 40.8; H, 6.9; N, 11.8%; $C_8H_{16}N_2O_4S$ requires: C, 40.7; H, 6.8; N, 11.9%; m/e 254 $(M+NH_4)^+$;

EXAMPLE 9

2-methyl-N-(nitromethylsulphonyl)piperidine, obtained as an oil in 24.8% yield;* microanalysis, found: C, 38.2; H, 6.2; N, 12.6%; $C_7H_{14}N_2O_4S$ requires: C,37.8; H, 6.35; N, 12.6%; m/e 223 $(M+H)^+$;

EXAMPLE 10

4-benzyl-N-(nitromethylsulphonyl)piperidine, in 8.9% yield***, m.p. 57°–58° C. (ethanol); microanalysis, found: C, 52.3; H, 6.2; N, 9.4%; $C_{13}H_{18}N_2O_4S$ requires: C,52.3; H, 6.1; N, 9.39%; m/e 298 $(M^+)$;

[Notes: * Propyl nitrate used in place of isoamyl nitrate  Initial lithiation reaction carried out 10° to 12° C. and then cooled to −30° C. before addition of isoamyl nitrate. * Iso-butyl nitrate used in place of isoamyl nitrate.]

EXAMPLE 11

4-(nitromethylsulphonyl)-1-phenylpiperazine, in 16% yield, m.p. 146°–147° C. (ethanol); microanalysis, found: C, 46.7; H, 5.6; N, 14.3%; $C_{11}H_{15}N_3O_4S$ requires: C, 46.3; H, 5.3; N, 14.7%; m/e 286 $(M+H)^+$;

[Note: For Example 11, the initial lithiation reaction was carried out on a suspension of the starting methylsulphonyl derivative of formula V, and the reaction mixture was worked-up as follows:

The solvent was evaporated and the residue was partitioned as described in the general procedure but having water present in place of sodium hydroxide solution. The organic phase was treated with activated carbon and dried (MgSO$_4$), and the solvent was then evaporated to leave a yellow solid. The solid was partially purified by chromatography on 10 times its weight of silica gel (Merck Art 7734), eluting with methylene chloride. The crude product was dissolved in methylene chloride (150 ml), saturated sodium carbonate solution (60 ml) was added, and the mixture was vigorously stirred for 15 minutes. The precipitated sodium salt of the product was collected by filtration and washed successively with methylene chloride (30 ml), water (20 ml), ether (30 ml), methylene chloride (30 ml) and ether (20 ml). The resultant colourless solid was dissolved in warm water (100 ml), the solution was adjusted to pH 6 with acetic acid, and the mixture was then extracted with a mixture of ether (75 ml) and methylene chloride (145 ml). The organic phase was separated and the aqueous phase extracted with methylene chloride. The combined organic phases were washed with water (50 ml), treated with activated carbon and dried (MgSO$_4$), and the solvent was evaporated to give 4-(nitromethylsulphonyl)-1-phenylpiperazine (2.84 g, after recrystallisation from ethanol).]

EXAMPLE 12

4-methyl-1-(nitromethylsulphonyl)piperazine, in 6.7% yield; decomposes at 145° C. (methanol); microanalysis, found: C, 32.2; H, 5.7; N, 18.5%; $C_6H_{13}N_3O_4S$ requires: C, 32.3; H, 5.9; N, 18.8%; m/e 224 $(M+H)^+$.

[Note: For Example 12, following the extraction of the product into alkaline aqueous solution and acidification to pH 5–6, exhaustive extraction with methylene chloride was required to isolate the product.]

The starting methylsulphonyl derivatives of formula V required for the above Examples were obtained as follows:

A solution of the appropriate cyclic amine (0.10 mole) and triethylamine (10.12 g, 13.9 ml, 0.10 mole) in toluene (150 ml) was stirred at 5°–10° C. during the dropwise addition of a solution of methanesulphonyl chloride (11.46 g, 7.74 ml, 0.10 mole) in toluene (50 ml) during about 1 hour. The mixture was allowed to warm to ambient temperature, stirred for 16 hours, acidified by adding 2M hydrochloric acid (30 ml) and then treated by one of the following alternatives:

(a) In some cases (preparations 1, 2, 4, 5 and 8–10 below) two clear layers were obtained. The organic layer was separated, washed with water, dried (MgSO$_4$) and the solvent evaporated to give the methylsulphonyl derivative as a solid.

(b) In other cases (preparations 3, 6 and 7 below) a two phase slurry was obtained which was converted to clear layers by addition of ethyl acetate (100 ml) or methylene chloride (100 ml) and warming the mixture to about 35° C. The organic layer was then separated washed with water, dried (MgSO$_4$) and evaporated to give the methylsulphonyl derivative as a solid.

(c) In certain cases (preparations 3 and 6), removal of the solid by filtration of the two phase slurry gave some of the methylsulphonyl derivative as a solid, after washing with toluene, then with water and air-drying. The remaining material was obtained from the organic layer in the filtrate and washings using the procedure of (a) above.

In general the methylsulphonyl derivatives were sufficiently pure to be used without special purification in the nitration procedure.

Using the above general procedure, the following methylsulphonyl derivatives were obtained:

(Preparation 1): N-methylsulphonylpiperidine, as a solid, m.p. 46°–48° C., in 89% yield starting from piperidine;

(Preparation 2): N-methylsulphonylpyrrolidine, as a solid, m.p. 68°–70° C., in 69% yield starting from pyrrolidine;

(Preparation 3): 2-methylsulphonyl-1,2,3,4-tetrahydroisoquinoline, as a solid, m.p. 125°–126° C. (recrystallised from ethanol), in 84% yield starting from 1,2,3,4-tetrahydroisoquinoline;

(Preparation 4): 1-methylsulphonyl-1,2,3,4-tetrahydroquinoline, as a solid, m.p. 77°–78° C., in 99% yield starting from 1,2,3,4-tetrahydroquinoline;

(Preparation 5): N-methylsulphonyl-4-phenylpiperidine, as a solid, m.p. 129°–131° C., in 74% yield starting from 4-phenylpiperidine;

(Preparation 6): N-methylsulphonylthiomorpholine, as a solid, m.p. 128°-131° C., in 91% yield starting from thiomorpholine;

(Preparation 7): N-methylsulphonylthiazolidine, as a solid, m.p. 75°-78° C., in 83% yield starting from thiazolidine;

(Preparation 8): 2,6-dimethyl-N-methylsulphonylpiperidine, as a solid, m.p. 59°-62° C., in 63.4% yield starting from 2,6-dimethylpiperidine;

(Preparation 9): 2-methyl-N-methylsulphonylpiperidine, as an oil, in 96% yield starting from 2-methylpiperidine;

(Preparation 10): 4-benzyl-N-methylsulphonylpiperidine, as a solid, m.p. 91°-93° C., in 92.2% yield starting from 4-benzylpiperidine;

(Preparation 11): 4-methylsulphonyl-1-phenylpiperazine, as a solid, m.p. 181.5°-183.5° C., in 93.2% yield starting from 1-phenylpiperazine. [In this case, the work-up required addition of water (100 ml) in place of 2M hydrochloric acid, and methylene chloride (250 ml), followed by warming, to give two clear layers, from which the product was isolated as described in (a)];

(Preparation 12): 4-methyl-1-methylsulphonylpiperazine, as a solid, m.p. 94.5°-95.5° C., in 33.7% yield starting from 1-methylpiperazine. [In this case, the work-up required addition of 2M NaOH (50 ml) in place of 2M Hydrochloric acid and methylene chloride (70 ml), followed by filtration through a cotton wool plug to give two clear layers, from which the product was isolated as described in (a)].

EXAMPLES 13-18

Using a similar procedure to that described in Example 1, the following compounds of formula I were obtained:

EXAMPLE 13

N-(nitromethylsulphonyl)-3,4-dehydropiperidine, in 14% yield, *** m.p. 56.5°-57.5° C. (10:6 v/v ethanol: water); microanalysis, found: C,35.3; H,5.0; N,13.4%; $C_6H_{10}N_2O_4S$ requires: C,35.0; H,4.9; N,13.6%; m/e 206 (M)+;

(EXAMPLE 14)

N-(nitromethylsulphonyl)homopiperdine, in 24% yield,*** m.p. 111.5°-112.5° C. (5:1 v/v ethanol:water); microanalysis, found: C,38.0; H,6.3; N,12.4%; $C_7H_{14}N_2O_4S$ requires: C,37.8; H,6.4; N,12.6%; m/e 222 (M+H)+;

(EXAMPLE 15)

N-(nitromethylsulphonyl)indoline, in 19% yield,*** m.p. 85.5°-86.5° C. (ethanol); microanalysis, found: C,45.0; H,4.3; N,11.6%; $C_9H_{10}N_2O_4S$ requires: C,44.7; H,4.1; N,11.6%; m/e (chemical ionisation) 260; $(M+NH_4)^+$.
[Note: *** Isobutyl nitrate used in place of isoamyl nitrate].

(EXAMPLE 16)

N-(nitromethylsulphonyl)-2-methylindoline, in 17% yield, obtained as an oil after chromatography eluting with 25% ethyl acetate in 60°-80° C. petrol; microanalysis, found: C,46.2; H,4.7; N,10.7%; $C_{10}H_{12}N_2O_4S.\frac{1}{4}$ $H_2O$ requires: C,46.1; H,4.8; N,10.7%' m/e 255 (M-H).

(EXAMPLE 17)

N-(nitromethylsulphonyl)-3,5-cis-dimethylmorpholine, in 4% yield, m.p. 166°-167° C. (recrystallised twice from ethanol); microanalysis, found: C,35.4; H,5.6; N,11.6%; $C_7H_{14}N_2O_5S$ requires: C,35.3; H,5.9; N,11.8%; m/e 237 (M-H).

In this Example chloroform replaced methylene chloride as the chromatography solvent.

(EXAMPLE 18)

N-(nitromethylsulphonyl)isoindoline, in 10.7% yield, m.p. 179°-180° C. (ethanol); microanalysis, found: C,44.3; H,3.8; N,11.2%; $C_9H_{10}N_2O_4S$ requires: C,44.6; H,4.1; N,11.6%; m/e 241 (M-H).

The starting methylsulphonyl derivatives of formula V required for the above Examples were obtained as described in connection with Examples 1-12 above:

(Preparation 13): N-(methylsulphonyl)-3,4-dehydropiperidine, as a solid, m.p. 56°-58° C. in 60.4% yield starting from 3,4-dehydropiperidine;

(Preparation 14): N-(methylsulphonyl)homopiperidine, as a solid, m.p. 44.5°-46.5° C. in 83.4% yield from homopiperdine;

(Preparation 15): N-(methylsulphonyl)indoline, as a solid, m.p. 65°-65.5° C. in 96% yield from indoline.

(Preparation 16): 2-methyl-N-(methylsulphonyl)indoline, as a solid, m.p. 51°-52° C. in 63% yield (obtained in this example after chromatography on silica eluted with 25% ethyl acetate/60°-80° C. petroleum ether) from 2-methylindoline.

(Preparation 17): cis-3,5-dimethyl-N-(methylsulphonyl)morpholine, as a solid, m.p. 158° C. in 53% yield (after 1 recrystallisation from chloroform and after 2 recrystallisations from ethanol) from 3,5-dimethylmorpholine which was a mixture of cis- and trans-isomers.

(Preparation 18): N-(methylsulphonyl)isoindoline, as a solid, m.p. 131°-132° C. in 96% yield, obtained as follows:

Methanesulphonamide (4.8 g) was added in portions to a stirred suspension of 60% w/w sodium hydride dispersion in oil (4.0 g-previously washed with 60°-80° C. petrol to remove the oil) in dry DMF (80 ml). The mixture was stirred at 60° C. for 1 hour then at room temperature for 2 hours. 1,2-Di(chloromethyl)benzene (8.75 g) was added in portions over 15 minutes and the reaction mixture heated to 60° C. A delayed exotherm briefly took the temperature to 80° C. After 2 hours at 60° C., the mixture was poured onto crushed ice and the precipitated solid removed by filtration and dissolved in chloroform. The solution obtained was then dried ($MgSO_4$) and evaporated to leave the product (9.5 g) as a solid.

EXAMPLE 19

The following illustrate representative pharmaceutical dosage forms containing a compound of the formula I, for example a compound exemplified hereinbefore, or a non-toxic salt thereof (hereafter referred to as "compound X"), for therapeutic or prophylactic use in humans:

| (a) Tablet I | mg/tablet |
|---|---|
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |
| (b) Tablet II | mg/tablet |

-continued

| | |
|---|---|
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| d) Capsule | mg/capsule |
|---|---|
| Compound X | 10 |
| Lactose Ph. Eur | 488.5 |
| Magnesium stearate | 1.5 |

| (e) Injection I | (50 mg/ml) |
|---|---|
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Compound X | 1.0% w/v |
| Sodium phosphate BP | 3.6% w/v |
| 0.1M Sodium hydroxide solution | 15.0% v/v |
| Water for injection to 100% | |

| (g) Injection III | (1 mg/ml, buffered to pH 6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

Note
The above formulations may be obtained by conventional procedure well known in the pharmaceutical art. The tablets (a)-(c) may be enteric coated by conventional means for example to provide a coating of cellulose acetate phthalate.

The active ingredient X may also be replaced by the known compound N-(nitromethylsulphonyl)morpholine or a pharmaceutically acceptable salt thereof.

CHEMICAL FORMULAE

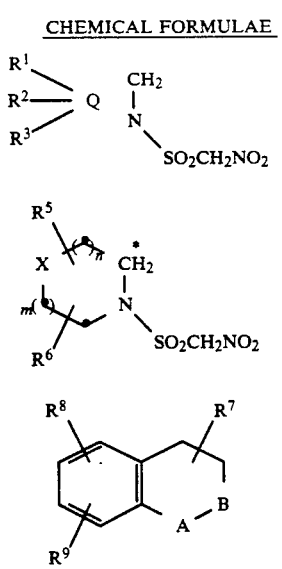

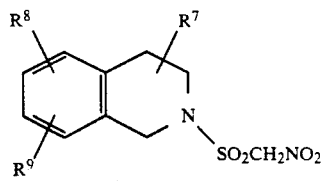

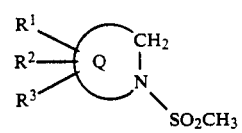

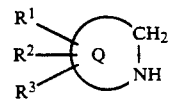

What is claimed is:

1. A heterocyclic compound of the formula I

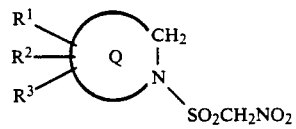

wherein ring Q together with two of $R^1$, $R^2$ and $R^3$ forms an isoindoline moiety and the third of $R^1$, $R^2$ and $R^3$ is hydrogen; and wherein the benzene ring of said isoindoline moiety itself optionally bears 1 or 2 substituents independently selected from the group consisting of, halogeno, hydroxy, (1-6C)alkyl, (1-6C) alkoxy, phenyl, phenoxy and phenyl (1-4C)alkyl, the last three of which may themselves optionally bear 1 or 2 substituents independently selected from the group consisting of halogeno, trifluoromethyl, (1-4C)alkyl and (1-4C)alkoxy; or a pharmaceutically acceptable salt thereof.

2. A compound as claimed in claim 1 wherein the benzene ring of the isoindoline moiety itself optionally bears 1 or 2 substituents independently selected from fluoro, chloro, bromo, iodo, hydroxy, methyl, ethyl, isopropyl, propyl, butyl, methoxy, ethoxy, propoxy, butoxy, t-butoxy, phenyl, phenoxy, phenylmethyl, 1-phenylethyl and 2-phenylethyl, the last five of which may themselves optionally bear 1 or 2 substituents independently selected from the group consisting of fluoro, chloro, bromo, iodo, trifluoromethyl, methyl, ethyl, isopropyl, propyl, methoxy, ethoxy and propoxy.

3. A compound according to claim 1 which is N-(nitromethylsulphonyl)isoindoline, or a pharmacuetically acceptable salt thereof.

4. A pharmaceutical composition which includes an active ingredient selected from a compound of the formula I as defined in claim 1 and the pharmaceutically acceptable salts thereof, together with a pharmaceutically acceptable diluent or carrier.

5. A method for inhibiting the enzyme aldose reductase in an animal requiring such inhibition which comprises administering to said animal an amount of a compound of formula I, or a pharmaceutically acceptable salt thereof, as defined in claim 1, effective to inhibit said enzyme.

* * * * *